United States Patent [19]

Fuxue et al.

[11] Patent Number: 4,846,178

[45] Date of Patent: Jul. 11, 1989

[54] ELECTRIC FIELD THERAPEUTIC APPARATUS

[75] Inventors: Zhang Fuxue; Zhu Weitong; Yang Xiufeng, all of Beijing, China

[73] Assignee: Beijing Information Technology Institute, Beijing, China

[21] Appl. No.: 48,039

[22] Filed: May 11, 1987

[30] Foreign Application Priority Data

Jun. 5, 1986 [CN] China .................................. 86103803

[51] Int. Cl.⁴ .............................................. A61N 1/40
[52] U.S. Cl. ................................ 128/419 F; 128/422; 128/798; 128/802
[58] Field of Search .................. 128/420 R, 421, 422, 128/423 R, 419 F, 783, 798, 802

[56] References Cited

U.S. PATENT DOCUMENTS

| | | | |
|---|---|---|---|
| 3,785,383 | 1/1974 | Dotto | 128/804 |
| 3,881,494 | 5/1975 | Paul, Jr. | 128/421 |
| 3,915,151 | 10/1975 | Kraus | 128/419 F X |
| 4,093,975 | 6/1978 | Roberts | 128/422 UX |
| 4,116,238 | 9/1978 | Pettijohn | 604/20 |
| 4,580,570 | 4/1986 | Sarrell et al. | 128/421 |
| 4,676,246 | 6/1987 | Korenaga | 128/783 X |

FOREIGN PATENT DOCUMENTS

| | | | |
|---|---|---|---|
| 1181826 | 11/1964 | Fed. Rep. of Germany | 128/798 |
| 1045883 | 10/1966 | United Kingdom . | |
| 1321310 | 6/1973 | United Kingdom . | |
| 1350937 | 4/1974 | United Kingdom . | |
| 1485709 | 9/1977 | United Kingdom . | |
| 2128093 | 4/1984 | United Kingdom . | |
| 2183158 | 6/1987 | United Kingdom . | |

*Primary Examiner*—Lee S. Cohen
*Attorney, Agent, or Firm*—Ladas & Parry

[57] ABSTRACT

An electric field therapeutic apparatus comprising a D.C. source, an oscillator, a transformer, a rectificating circuit and output electrodes isolated from the environment for creating an electric field adjacent an injured part of a human or animal body to fulfil therapeutic purposes. The electric field is of a potential adjustable within a range of 100-5,000 V, and by adapting a pulse generator, and a switching circuit, this electric field can be formed by a pulse signal or pulse modulated alternating signal. The isolated electrodes can be combined with the conventional splint or bandage according to its different designs.

8 Claims, 6 Drawing Sheets

ELECTRIC FIELD THERAPEUTIC APPARATUS

BACKGROUND OF THE INVENTION

The present invention relates to an electric field therapeutic apparatus, and more particularly, to an apparatus which can provide a high potential (100–5,000V) electric field to an injured site of a human or animal body via electrodes isolated electrically from the environment, so as to promote healing of injured tissues such as fractured bone and wounded soft tissues.

The piezoelectric effects of bone, muscle and other soft tissues of human and animal body have long been researched by the medical and piezoelectric researchers. Generally speaking, the biopolymers, like all the other piezoelectric materials, exhibit the piezoelectric effects, namely, they will be electrically is understood that the researching and utilizing of the biopolymer's piezoelectric effect are of significant importance for understanding the mechanism of a living body's growth and for promoting the biomedical progress. The inventors of the present invention have made an extensive effort in this field, one of the inventors Mr. Zhang Fuxue, is the coauthor of the book "PIEZOELECTRICITY", published by Defence Industry Publishing House, Beijing, 1984. The disclosure of Chapter 30, Volume II, PP 623-673 of this book is incorporated herewith by reference.

It is known from the above-mentioned book that the experiments have been made to show that a human or animal bone is charged with negative electricity on its surface when it is oppressed by external stress, it is further proved that a bone with negative charge will exhibit an active growth, and similar thing can happen to other soft tissues. It is believed that a change of the electrical environment at a bone fracture will promote the healing of the fractured bone and other injured tissues, and the piezoelectric effect of the bone and other tissues contribute to this healing. The phenomena of a bone's piezoelectric effect are used to explain why physical exercises promote the metabolism of bone tissue and accelerate the healing of injured tissues. On the other hand, since the piezoelectric effect is reversible, it suggests that if an external electric field is formed adjacent a bone fracture, it can also accelerate the healing of injured tissues.

According to what is mentioned above, a foil electret is used to form an external electric field adjacent a bone fracture, so as to promote the healing of the fractured bone. Reference can be made to "Promote Healing of Bone by Using Electret", by Wang Shoutai, STATIC ELECTRICITY TECHNIQUE, volume 1, 1984 PP 1–5. The problems of this method are that the electrical charge of a foil electret will be lost after some time, so that electret must be replaced regularly during the therapeutic period, and on the other hand, the range of the electric field strength produced by electret is too narrow and uncontrollable, so that strength of the electric field can not be adjusted to meet the patients' different conditions in clinical practice. All these problems made it difficult to use the electret widely in clinical practice.

In prior art, there is a kind of apparatus for healing fractured bone with interacting electric current and a magnetic flux field. This apparatus generates electric current pulses and magnetic field pulses to produce a net current in the region of the fractured bone and generally perpendicular to the plane of the fracture, as disclosed in U.S. Pat. No. 4,556,051, by Maurer.

It is known in the art that during the therapeutic period of injured tissues, especially fractured bone, there exists a contradiction between the fixing and moving of the injured body part. On one hand, the fractured bone should be well fixed to keep the fracture aligned and heal, that means to avoid any movement of the injured body part such as an injured limb, this is usually done by using plaster. On the other hand, during the relatively long time of this period, the blood circulation at the fixed part will be reduced and a local under-nutrition happens, the piezoelectric effect of the injured tissue will decrease because of lacking mechanical stress caused by body movement, all these will jeopardize the electrical environment of the bone fracture and result in myatrophy and arthocleisis of the injured body part, therefore, make the patient suffering more and longer.

SUMMARY OF INVENTION

On the basis of the piezoelectric effect of the bone, muscle and other soft tissue of human and aminal body, the present invention provides an electric field therapeutic apparatus which can form a relatively strong electric field adjacent the injured part of a human or animal body, the electric potential between the output electrodes can be, for example, in the range of 100–5,000V. By the effects of this electric field, it will happen the polarization of biopolymers and the rearrangement and movement of the electric dipoles within living tissues, thereby improving the electrical environment of the injured tissues, solving the problems caused by the decreased piezoelectric effect in the injured tissues per se, and making the injured tissues grow actively. In addition, by using specially designed circuit and output electrodes, the apparatus of the invention can be used for fixing the fractured bone and being carried out everywhere by the patient, especially for doing physical exercises therapy, this provides a great convenience to its users.

According to a prefered embodiment of the invention, an electric field therapeutic apparatus comprises: an electric source which can be a battery or any conventional a.c. to d.c. converting circuit; an oscillating circuit which can convert the d.c. output of the source into an alternating signal of specific frequency; a transformer, preferably a piezoelectric transformer, which transforms the alternating output of the oscillating curcuit into a high voltage signal; a rectificating circuit, such as a voltage doubler, which can change the high voltage alternating output of the transformer into a high voltage directive signal; and output electrodes which are isolated from the environment so as to form a static electric field. The piezoelectric transformer is adapted in the apparatus of the present invention to generate a highvoltage/micro-current output, to provide a high output, resistance, and to reduce the volume and weight of the apparatus. By using adjustable components in the circuit, the electric potential between the output electrodes can be adjusted within a range of 100–5,000V, and the static electric field formed by this potential is applied to an injured body part where the treatment is needed, through electrodes isolated from the body. The shape, structure, dimension, material and rigidity of the electrodes can all be selected and changed according to patient's different conditions. The output electrodes of the invention can be easily combined with the conventional splint or bandage, that makes the present apparatus can be widely used in clinical practice.

According to another prefered embodiment of the invention, an electric field therapeutic apparatus comprises: an electrical source which can be a battery or any conventional a.c. to d.c. converting circuit; a pulse generator which generates low frequency pulse signals; an oscillating and transforming circuit wherein a ferrite transformer is preferably adapted to generate an output signal modulated by the pulse signals of the pulse generator; a switching circuit; a voltage multiplier; a step-up transforming circuit; wherein the switching circuit selectively connects the output of the oscillating and transforming circuit to the voltage multiplier or the step-up transforming circuit, so as to generate a high voltage directive or alternating output respectively; and composite circuit which connects the directive output of the voltages multiplier or the alternating output of the step-up transforming circuit to output electrodes which are electrically isolated from the environment, so as to form an electric field for therapeutic purposes. By using the pulse generator and the switching circuit in this embodiment, it is possible to form, via the isolated output electrodes, an electric field which changes its strength at a low frequency in the range of 0.1–100 Hz, or form an alternating electric field with a frequency in the range of 10–100 KHz, therefore, different kinds of electric field can be applied to injured tissues according to patient's different condictions.

Since the apparatus of the present invention can be made small-sized and light-weight, it is convenient for patient to carry it out everywhere for doing all kinds of physical exercises, and since its output signals can be selected in different form and strength and its high output resistance keeps its output current small under any circumstances, it is safe for its user even if an isolating problem occurs. The therapy performed by the apparatus of this invention will be more effective if it is combined with physical exercise therapy to increase local blood circulation and piezoelectric effect of the injured tissues, therefore, it can make the therapeutic period shorter and avoid myatrophy and arthrocleisis, which usually happens during the therapy of fractured bone and the like, and is also helpful in the functional training and recovery after an orthopaedic operation.

The other objects, features and advantages of the invention will become more apparent in the following detailed description of the prefered embodiments of the invention, referring to the accompanying drawings in which like numerals represent like components or parts of the apparatus.

DETAILED DESCRIPTION OF PREFERED EMBODIMENTS

Figure 1:
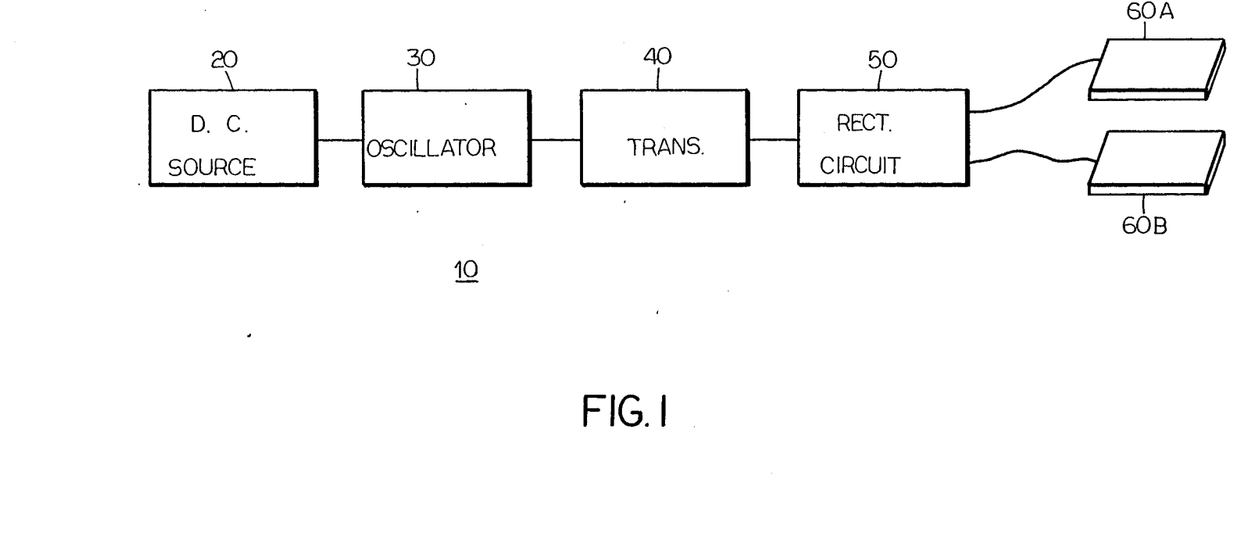
FIG. 1 is a block diagram which shows illustratively an exemplary embodiment of the invention.

Referring to FIG. 1, there is shown a block diagram of an exemplary embodiment of the electric field therapeutic apparatus according to the invention. In FIG. 1, numeral 10 represents the apparatus as a whole, numeral 20 indicates an electrical source which can be a battery or any conventional a.c. to d.c. converting circuit for providing directive current to the other parts of the apparatus. Numeral 30 indicates an oscillator formed by any conventional oscillating circuit which takes the directive current provided by source 20 as input and generates an alternating output of a specific frequency. Numeral 40 indicates a transformer which can be any conventional type, but a piezoelectric transformer is preferable, so as to meet the requirements of high output voltage, small output current and large output resistance of the present apparatus, all these requirements gaurantee the safty of such a high voltage use. When a piezoelectric transformer is adapted, the operating frequency of the oscillator 30 should be the same as the resonance frequency of the transformer 40 to keep it working at high efficiency, usually, this frequency is selected from the range of 10–100 KHz. Numeral 50 indicates a rectificating circuit, such as a voltage doubler, which changes the high voltage alternating output of the transformer 40 into a high voltage directive output, and then provides it to the injured part of a human body through the output electrodes 60A and 60B. In FIG. 1, electrode 60A is a positive one and 60B a negative one, their structure and usage will be further described hereinbelow.

Figure 2:
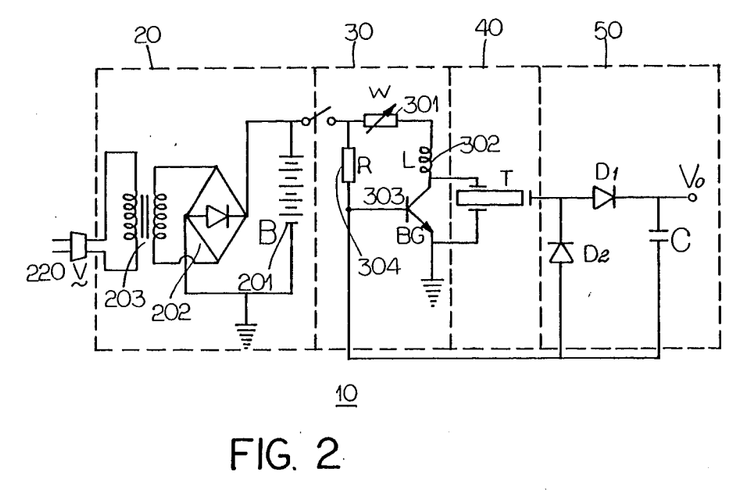
FIG. 2 shows the detailed circuit of the embodiment shown in FIG. 1.

Referring to FIG. 2, there is shown the detailed circuit of the embodiment shown in FIG. 1. In FIG. 2, the dashed line block 20 indicates the electrical source which comprises a battery 201 and a transforming and recitificating circuit made up of a bridge circuit 202 and a transformer 203, obviously any other kind of d.c. source can be used for the same purposes. The dashed line blocks 30 and 40 indicate respectively an oscillator and a piezoelectric transformer, they can be replaced by any other kind of piezoelectric step-up transforming circuit, but the operating frequency of the oscillator 30 should be selected the same as the resonance frequency of the piezoelectric transformer 40, so as to make it work efficiently, usually, this frequency is selected from the range 10–100 KHz. The adjustable resistor 301 of the oscillator 30 forms the voltage adjusting component of the apparatus. When the resistance of resistor 301 is changed the output voltage of the oscillator 30 will be changed and so will be the output voltage at electrodes 60A and 60B, so it is continuously adjustable within the range of, for example, 100–5,000 V. The dashed line block 50 indicates a rectificating circuit, such as a voltage doubler, if a higher output is necessary, a corresponding voltage multiplier can be used. Obviously, any other kind of rectificating circuit can be used for the same purposes.

Figure 3:
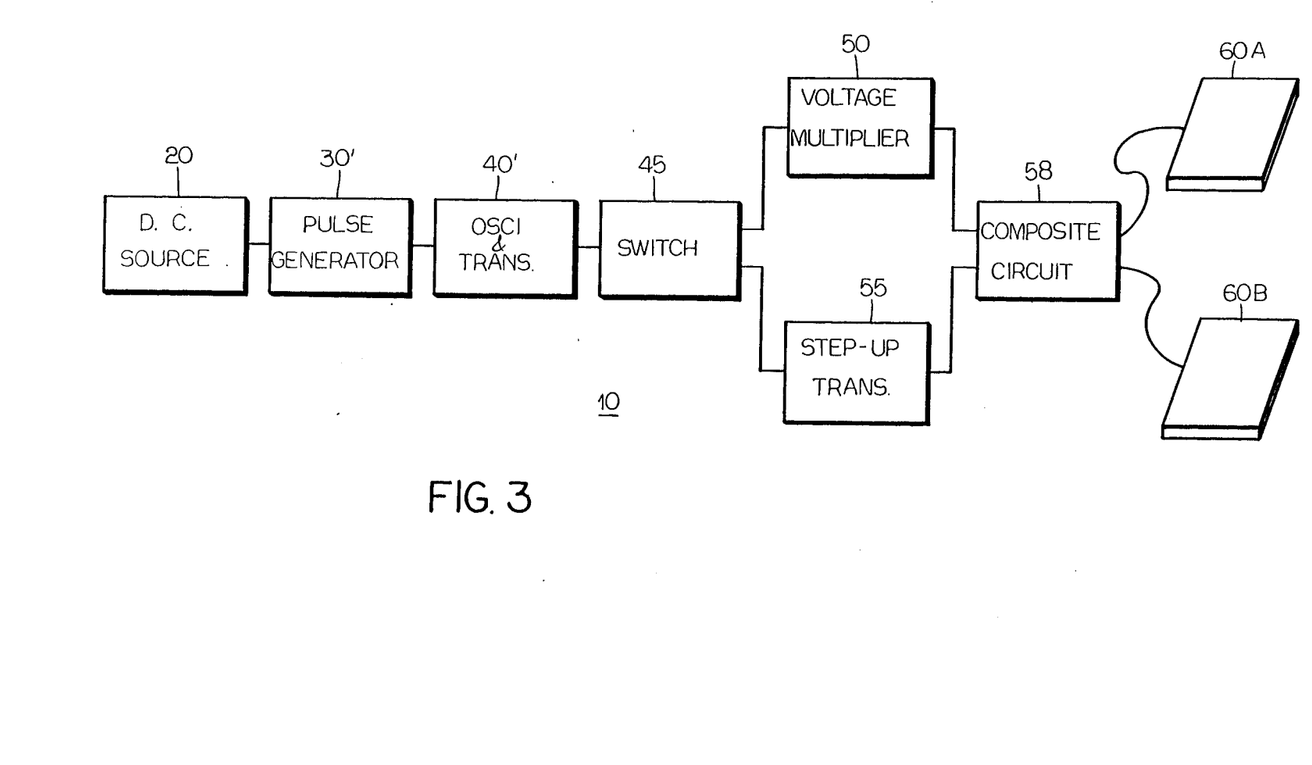
FIG. 3 is a block diagram which shows illustratively another exemplary embodiment of the invention.

Referring to FIG. 3, there is shown a block diagram of another embodiment of the invention. In FIG. 3, numeral 10 represents the apparatus as a whole. Numeral 20 indicates an electrical source which can be a battery or any conventional a.c. to d.c. converting circuit for providing directive current to the other parts of the apparatus. Numeral 30' indicates a pulse generator which generates low frequency pulse signals in the range of 0.1–100 Hz. Numeral 40' indicates an oscillating and transforming circuit wherein a ferrite transformer is preferably adapted to generate an output signal modulated by the pulse signals of the pulse generator 30'. Numeral 45 indicates a switching circuit which can selectively connect the output of the circuit 40' to a voltage multiplier 50 or a step-up transforming circuit 55, so as to generate a high voltage directive or alternating output respectively. Numeral 58 indicates a composite circuit which connects the directive output of the voltage multiplier 50 or the alternating output of the step-up transforming circuit 55 to the output electrodes 60A and 6B which are electrically isolated from the environment, so as to form an electric field for therapeutic purposes.

Figure 4:
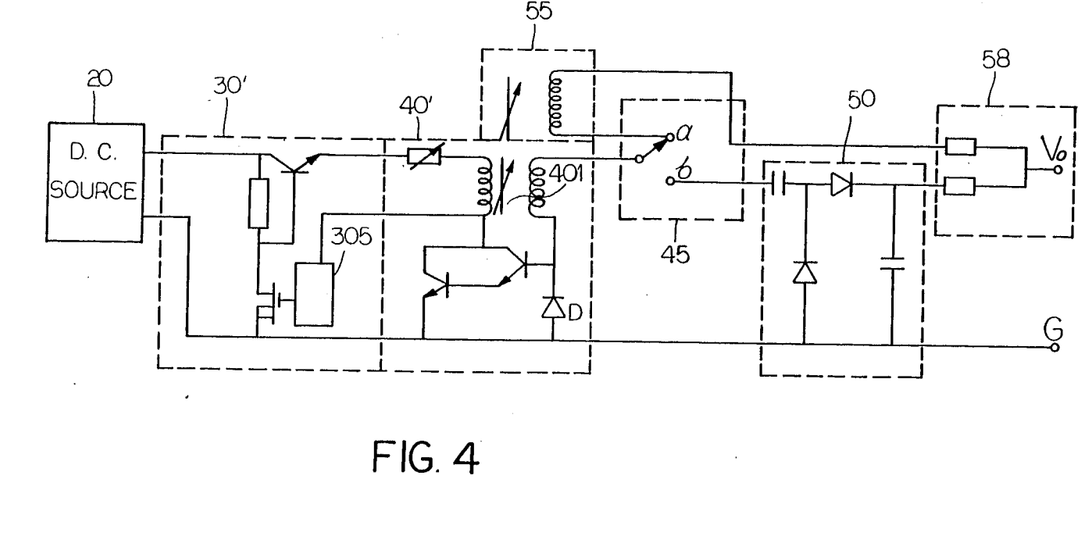
FIG. 4 shows the detailed circuit of the embodiment shown in FIG. 3.

Referring to FIG. 4, there is shown the detailed circuit of the embodiment shown in FIG. 3. In FIG. 4, the dashed line block 30' indicates a pulse generator which includes a timer 305, the pulse generator 30' generates a pulse signal with its frequency in the range of 0.1–100 Hz. The dashed line block 40' indicates an oscillating and transforming circuit wherein a frerrite transformer 401 works both as a transforming component and as an inductive component of the oscillating circuit, a diode D works as protection means for the transistors of the oscillating circuit. The dashed line block 45 indicates a switching circuit which has two positions a and b. When position a is connected, the output of circuit 40' will be connected to a step-up transforming circuit 55, which is part of the ferrite transformer 401, of course, it can also be another transformer, When position b is connected, the output of circuit 40' will be connected to a voltage multiplier 50, which converts the output of circuit 40, into a directive output. The output of the voltage multiplier 50 or the step-up transforming circuit 55 will pass a composite circuit 58 and connected to an output electrode as the output voltage $V_0$. It should be pointed out that by adapting the pulse generator 30' which generates a low frequency pulse signal, the oscillating singal of the circuit 40' is modulated by this pulse signal and so are the outputs of circuits 50 and 55. Therefore, the output voltage of this embodiment is either a directive pulse signal or an alternating signal modulated by a low frequency pulse signal.

Figure 5A:
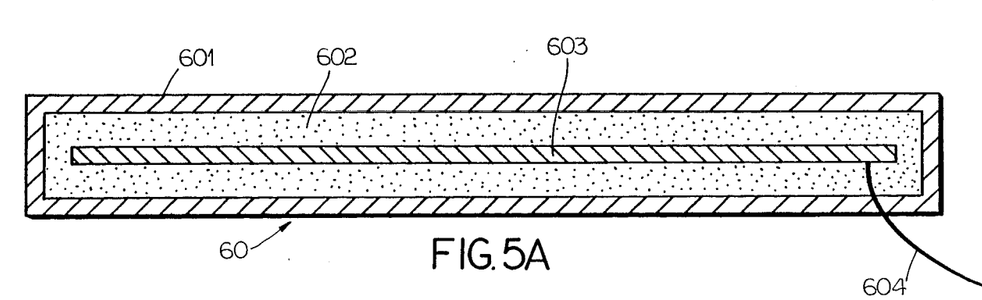
FIGS. 5A and 5B show illustratively the structure of the output electrodes shown in FIGS. 1 and 3.

FIG. 5A shows the detailed structure of the electrodes 60A and 60B shown in FIGS. 1 and 3, since they are the same in structure, only one of then will be described hereinbelow. In FIG. 5A, numeral 60 represents the electrode as a whole. Numeral 601 indicates a protecting layer made of soft, porous and disposable material, such as cloth, plastic foam or soft paper, it is adapted to protect skin from the injury of the electrode. Numeral 602 indicates an isolating layer made of an isolating or insulating film having a dielectric coefficient greater than 10 KV/mm, it is adapted to keep the electrode isolated from the environment and patient's body to form an electric field but no current will stimulate the patient. Numeral 603 indicates a conductive layer which forms the electric field for the therapeutic purposes, the layer 603 can be made of a metal sheets, foil, net or the like. Numeral 604 indicates a wire which connects the conductive layer 603 to the output of the circuit 50 in FIGS. 1 and 3 or circuit 58 in FIG. 3. Different kinds of electrodes can be made by selecting different materials for isolating layer 602 and conductive layer 603, so as to make the electrode rigid or flexible. The flexible electrode can be advantageously changed its shape to make a conformable contact with the surface of the injured body part, so as to form an even electric field over the body part to be treated.

Figure 5B:
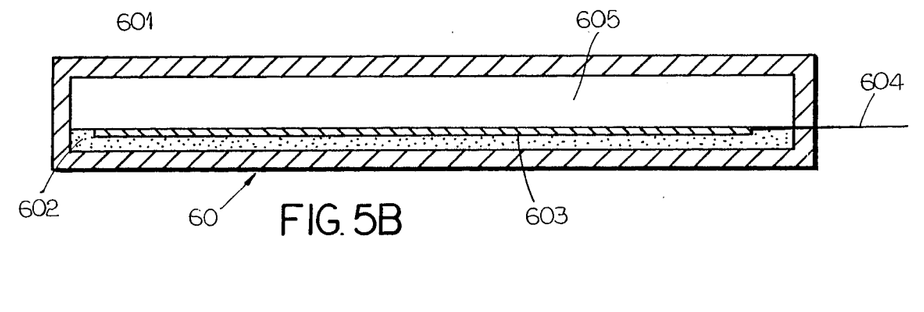

FIG. 5B shows another detailed structure of the electrodes 60A and 60B shown in FIGS. 1 and 3. The difference between this one and that of FIG. 5A is a supporting member 605 which is storing enough to be used as a splint for fixing a fractured bone.

Figure 6A:
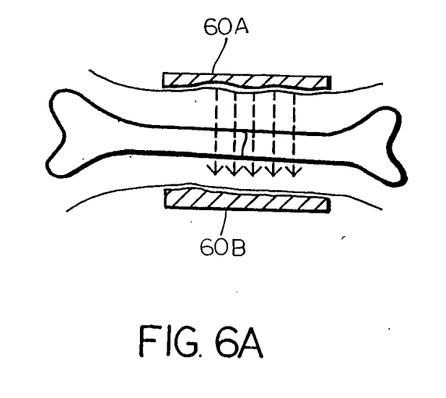
FIGS. 6A and 6B show illustratively the ways of arranging electrodes adjacent the bone fracture of a patient to form the electric field.
Figure 6B:
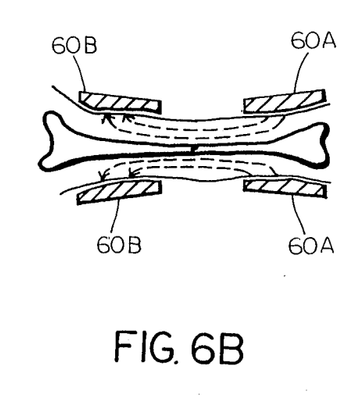

Referring to FIGS. 6A and 6B, there are shown two different ways of arranging the electrodes 60A and 60B adjacent a bone fracture. In FIG. 6A, a positive electrode 60A and a negative electrode 60B are arranged at the opposite two sides of a bone fracture, the direction of the electric field formed thereby is perpendicular to the length of the bone, this is called a transverse electric field treatement. In FIG. 6B, two flexible electrodes 60A and 60B are respectively surrounded on the near and far ends of the fractured bone with the bone fracture kept in between, the direction of the electric field formed thereby is parallel with the length of the bone, this is called a longitudinal electric field treatment. In FIGS. 6A and 6B, the direction of electric field is shown by the arrow and dashed line. The two electrodes 60A and 60B are respectively connected to the output terminals of the apparatus. In practical use, the patients, body can be connected to the ground of the apparatus and let the other electrode form the electric field adjacent the injured body part, and the two ways of arranging the electrodes can be combined together.

The conception, structure and usage of the apparatus according to the invention have been disclosed hereinbefore in the detailed description of the prefered embodiments combined with the accompanying drawings, obviously, it is easy for those skilled in the art to make many different modifications and rearrangements of the embodiments without departing the spirit of the invention, therefore, the scope of the present invention is only determined by the following claims.

What is claimed is:

1. An electric field therapeutic apparatus comprising:
 a D.C. source;
 oscillator means energized by said D.C. source for generating an alternating signal of specific frequency; means for transforming the alternating signal provided by said oscillator means into a voltage signal in the range of 100–5,000 V;
 means for rectifying the voltage signal provided by said transforming means to provide a direct current signal; and
 at least two insulated output electrodes connected to the rectifying means so as to form a static electric field, utilizing the direct current signal, adjacent to an injured body part to fulfil therapeutic purposes.

2. An apparatus according to claim 1, wherein said oscillator means includes an adjustable component for changing the output voltage of the apparatus within the range of 100–5,000V.

3. An apparatus according to claim 1, wherein the output electrodes comprise a conductive layer connected to said direct signal provided by said rectifying means, a supporting member at the back of the conductive layer and an insulating layer surrounding both the conductive layer and supporting member, said output electrodes are strong enough to be used as a spring for a fractured bone.

4. An apparatus according to claim 1 wherein the output electrodes are made up of a flexible conductive layer connected to said direct signal provided by said rectifying means, and a flexible insulating layer surrounding said conductive layer, whereby said output electrodes can made a conformable contact to the surface of the injured body part.

5. An electric field therapeutic apparatus comprising:
a D.C. source;
means for generating a pulse signal in the range of 0.1–100 Hz energized by said D.C. source;
oscillating and transforming means connected to said pulse generating means for generating an alternating signal of specific frequency under the control of said pulse signal;
voltage multiplier means for converting said alternating signal provided by said oscillating and transforming means into a direct pulse signal having a voltage in the range of 100–5,000V;
step-up transforming means for stepping up said alternating signal provided by said oscillating and transforming means to a voltage in the range of 100–5,000V;
switching means for selectively connecting said oscillating and transforming means to one of said voltage multiplier means and step-up transforming means;
composite circuit means for connecting said voltage multiplier means and said step-up transforming means to an output terminal; and
at least to insulated output electrodes connected to said output terminal for forming an electric field adjacent to an injured body part to fulfil therapeutic purposes.

6. An apparatus according to claim 5, wherein said oscillating and transforming means comprises an oscillating circuit and a transformer, said transformer also works as an inductive component of said oscillating circuit, and said step-up transforming means is the third coil of said transformer.

7. An apparatus according to claim 5, wherein said output electrodes comprise a conductive layer connected to said output terminal; a supporting member at the back of said conductive layer; and an insulating layer surrounding both the conductive layer and the supporting member, said output electrodes are strong enough to be used as a sprint for a fractured bone.

8. An apparatus according to claim 5, wherein said output electrodes are made up of a flexible conductive layer connected to said output terminal; and a flexible insulating layer surrounding said conductive layer, whereby said output electrodes make a conformable contact to the surface of the injured body part.

* * * * *